US011324303B2

(12) United States Patent
Vidotto et al.

(10) Patent No.: US 11,324,303 B2
(45) Date of Patent: May 10, 2022

(54) CLEANING HAIR TRIMMINGS AFTER CUTTING A PERSON'S HAIR

(71) Applicant: The Good Life Services LLC, Austin, TX (US)

(72) Inventors: Ryan Vidotto, Austin, TX (US); Deborah Vidotto, Austin, TX (US)

(73) Assignee: The Good Life Services LLC, Austin, TX (US)

(*) Notice: Subject to any disclaimer, the term of this patent is extended or adjusted under 35 U.S.C. 154(b) by 0 days.

(21) Appl. No.: 14/800,106

(22) Filed: Jul. 15, 2015

(65) Prior Publication Data

US 2016/0015153 A1 Jan. 21, 2016

Related U.S. Application Data

(60) Provisional application No. 62/025,283, filed on Jul. 16, 2014.

(51) Int. Cl.
| | |
|---|---|
| *A45D 44/16* | (2006.01) |
| *B08B 1/00* | (2006.01) |
| *B26B 19/38* | (2006.01) |
| *A61F 13/38* | (2006.01) |
| *A45D 44/08* | (2006.01) |
| *B65D 85/00* | (2006.01) |

(52) U.S. Cl.
CPC ............ *A45D 44/16* (2013.01); *A45D 44/08* (2013.01); *A61F 13/38* (2013.01); *B08B 1/003* (2013.01); *B26B 19/3833* (2013.01); *B65D 85/70* (2013.01); *A45D 2200/1018* (2013.01)

(58) Field of Classification Search
CPC .... A45D 44/16; A45D 44/08; B26B 19/3833; A61F 13/38; A61F 11/006
USPC ................................................ 604/1; 606/162
See application file for complete search history.

(56) References Cited

U.S. PATENT DOCUMENTS

| | | | |
|---|---|---|---|
| 4,646,364 A | 3/1987 | O Larey | |
| 6,012,463 A * | 1/2000 | Mitchell, Jr. | A45D 27/22 132/200 |
| 6,401,246 B1 | 6/2002 | Perez | |
| 6,420,024 B1 | 7/2002 | Perez et al. | |
| 6,629,329 B1 * | 10/2003 | Webb | B08B 1/00 15/209.1 |
| 8,173,857 B1 * | 5/2012 | Yananton | D04H 1/407 428/87 |
| 2004/0089316 A1 | 5/2004 | Hamilton et al. | |
| 2005/0095393 A1 | 5/2005 | Tabor-Cooper | |
| 2005/0267395 A1 * | 12/2005 | Mangold | D04H 1/425 604/1 |

(Continued)

FOREIGN PATENT DOCUMENTS

| | | |
|---|---|---|
| DE | 10304515 A1 | 8/2003 |
| EP | 1856288 B1 | 6/2011 |

(Continued)

*Primary Examiner* — Cris L. Rodriguez
*Assistant Examiner* — Brianne E Kalach
(74) *Attorney, Agent, or Firm* — Fish & Richardson P.C.

(57) ABSTRACT

Methods and products for cleaning hair trimmings after cutting a person's hair. One of the methods includes applying a microfiber swab to one of the person's ears to remove the loose hair trimmings resulting from cutting the person's hair. Another one of the methods includes attaching a microfiber neck strip to the person's neck prior to cutting the person's hair.

21 Claims, 5 Drawing Sheets

(56) References Cited

U.S. PATENT DOCUMENTS

| | | | |
|---|---|---|---|
| 2006/0169299 A1* | 8/2006 | Jansheski | A61C 15/046 132/323 |
| 2006/0200933 A1* | 9/2006 | McDonnell | A47L 13/20 15/247 |
| 2007/0141562 A1 | 6/2007 | Grove | |
| 2007/0299457 A1* | 12/2007 | Morales | A61F 11/006 606/162 |
| 2009/0044361 A1* | 2/2009 | Rash | A46B 5/00 15/210.1 |
| 2009/0250075 A1* | 10/2009 | Chard | A41D 27/16 132/200 |
| 2011/0174327 A1* | 7/2011 | Koehl | A61F 13/38 132/200 |
| 2011/0282243 A1* | 11/2011 | Nakatani | A45D 34/04 600/580 |
| 2012/0224967 A1* | 9/2012 | Radabaugh | F04D 25/088 416/62 |
| 2012/0283616 A1* | 11/2012 | Edme | A61F 11/006 604/1 |
| 2012/0316381 A1* | 12/2012 | Teggatz | A61M 35/003 600/9 |

FOREIGN PATENT DOCUMENTS

| | | |
|---|---|---|
| JP | 2005211356 A | 8/2005 |
| WO | WO2007075412 A3 | 11/2008 |

\* cited by examiner

CLEANING HAIR TRIMMINGS AFTER CUTTING A PERSON'S HAIR

CROSS REFERENCE TO RELATED APPLICATION

This application claims priority under 35 U.S.C. § 119 to U.S. Provisional Patent Application Ser. No. 62/025,283, filed Jul. 16, 2014, and entitled "CLEANING HAIR TRIMMINGS AFTER CUTTING A PERSON'S HAIR," the entire contents of which are hereby incorporated by reference.

BACKGROUND

In a barbershop, a barber will often cut a customer's hair using an electric trimmer. Trimmers are useful to cut hair uniformly to a certain length and especially to lengths which are not practical using traditional scissor cuts. However, trimmers can cause a significant number of small hairs to fall around the customer's head, neck, and shoulders. To keep customers looking clean and free of those small hairs, barbers use a number of tactics. For example, barbers can use a paper neck strip around a customer's neck to catch loose hairs, barbers can use a brush to brush loose hairs off of a customer, and barbers can use forced air systems to blow loose hairs off of a customer.

SUMMARY

This disclosure describes cleaning hair trimmings from a person's ears after cutting a person's hair. A barber or a hair stylist can use a microfiber swab to quickly remove substantial amounts of loose hair trimmings from a person's ears. This can be especially useful in barbershops or salons that serve customers, e.g., who are returning to work in an office setting, or who are on their way to an event where appearance matters.

Particular embodiments of the subject matter described in this disclosure can be implemented to realize one or more advantages. A barber or hair stylist can clean loose hair trimmings from a person's ears after a haircut. A microfiber swab can be used to quickly and comfortably remove most or all of the loose hair trimmings from the person's ears. The microfiber swab can then be discarded or recycled. The microfiber swabs can be vastly more effective than cotton swabs, e.g., because the microfiber swabs actually pick up the hair rather than just moving it around. Customers may want the hair removed so that the body does not produce excess wax to push hair out of the ear.

The microfiber swab can be in various shapes to accommodate preferences of particular barbers and hair stylists. The microfiber used in the swabs need not be lint free and packaged in sterile packaging, which can reduce the cost of the microfiber swabs compared to swabs used in, e.g., the microelectronic industry. The microfiber swabs can also be used to clean various other surfaces.

The details of one or more embodiments of the subject matter described in this disclosure are set forth in the accompanying drawings and the description below. Other features, aspects, and advantages of the subject matter will become apparent from the description, the drawings, and the claims.

BRIEF DESCRIPTIONS OF DRAWINGS

FIG. 2A is a diagram of an example product kit that could be produced and sold to barber shops, hair salons, and the like.

Like reference numbers and designations in the various drawings indicate like elements.

DETAILED DESCRIPTION

Figure 1:
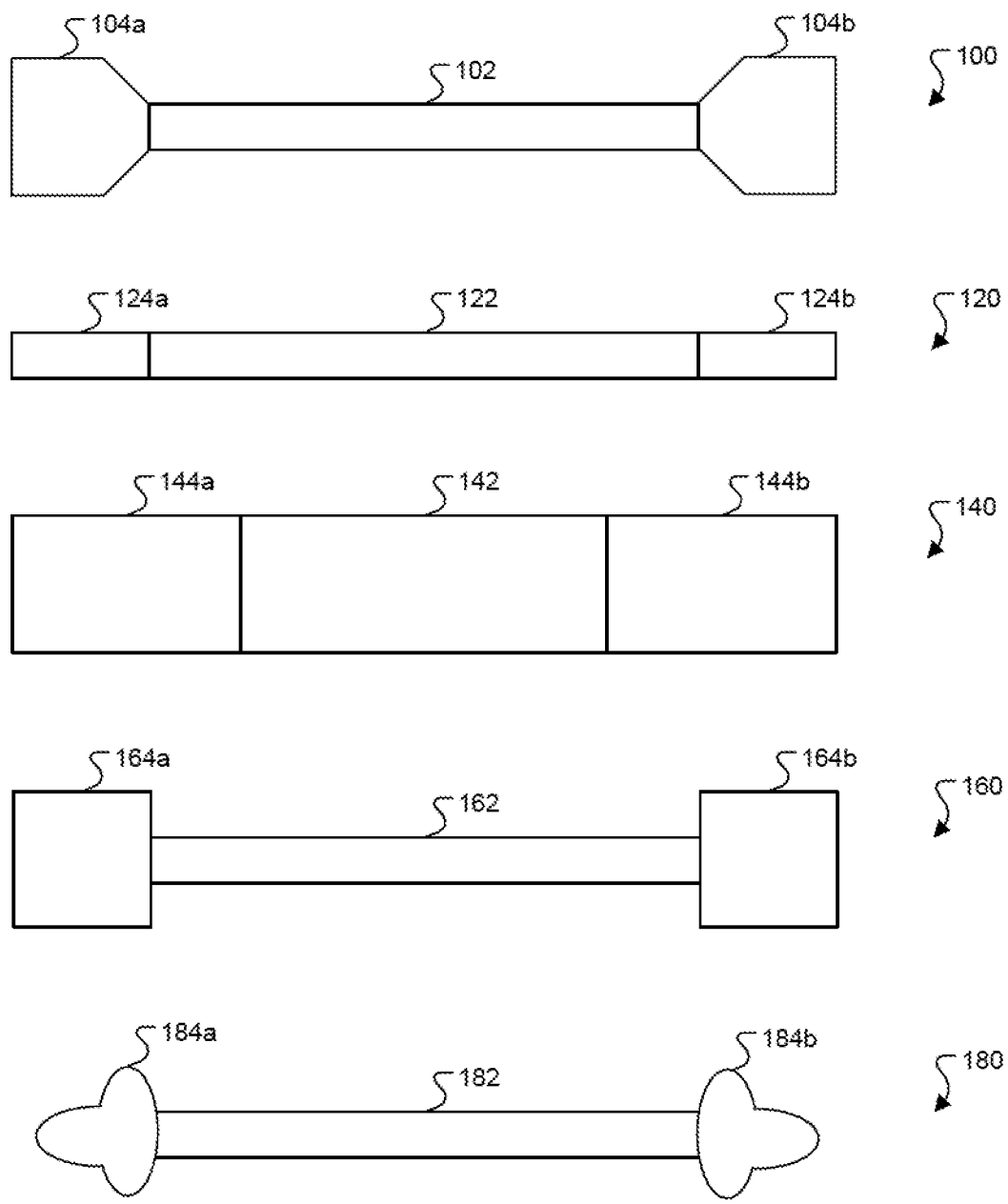
FIG. 1 is a diagram illustrating five example microfiber swabs for use in cleaning loose hair trimmings from a person's ears after a haircut.

FIG. 1 is a diagram illustrating five example microfiber swabs 100, 120, 140 and 160, 180 for use in cleaning loose hair trimmings from a person's ears after a haircut.

The first example swab 100 includes a handle 102, a first microfiber head 104a, and a second microfiber head 104b. The handle can be made from wood, pressed and rolled paper, plastic, or any appropriate material. The handle can be made from material that has a certain stiffness and is inexpensive and disposable or recyclable. The handle can be cylindrical, rectangular, or any other appropriate shape, and in some cases the handle can have a texture or gripping material applied to it to improve gripping.

The microfiber heads 104a-b are made from microfiber cloth. Microfiber cloth is made from a synthetic fiber, e.g., polyester, or a blend of polyester and polyamide. The microfiber cloth will generally be split during the manufacturing process to produce multi-stranded fibers, leaving a structure with fiber spaces that can be loaded with loose hair trimmings or dust or other substances. The microfiber cloth will generally also be electrostatic, e.g., by being positively charged. Due to the charge, the microfiber cloth can attract other substances having an electrostatic charge, e.g., loose hair trimmings.

The microfiber heads 104a-b can be attached to the ends of the handle in any appropriate way. For example, microfiber cloth can be wrapped around the ends and glued onto the handle. In another example, microfiber cloth can be sealed around the ends of the handle by ultrasonic welding or other industrial joining techniques. In some implementations, the microfiber cloth is secured to a shaping structure to give the microfiber heads 104a-b a certain shape. For example, the shaping structure can be a piece of cardboard which is joined to the handle.

Referring to the first example swab 100, the microfiber heads 104a-b are shaped into substantially flat, spade-shaped heads. Since the microfiber heads 104a-b are substantially flat, they can bend while being applied to a person's ears, so that the heads 104a-b can pick up loose hair trimmings without applying an uncomfortable pressure to the person's ears. The corners of the heads 104-ab can be rounded to reduce or eliminate any uncomfortable sharp edges.

The heads 104a-b in the first example swab 104a-b are wider than the handle 102, which can be useful, e.g., to reduce the amount of material needed for the handle while maintaining a broad micro fiber area to attract loose hair trimmings. The heads 104a-b also taper to the handle, which can be useful, e.g., to improve the ability to maneuver the heads inside of certain spaces.

The second example swab 120 includes a handle 122, a first microfiber head 124a, and a second microfiber head 124b. The second example swab 120 has a substantially uniform width across the swab from the first head 124a to the second head 124b. The microfiber heads 124a-b can be flat, cylindrical, spherical, or in any other appropriate shape. The corners of the heads 104a-b can be rounded. Compared to the first example swab 100, the second example swab 120 can, in some cases, require more material to manufacture due to an increased width of the handle. This can be useful, e.g., by making the handle easier to grip, easier to manufacture, and/or easier to fit into appropriate packaging.

The third example swab 140 includes a handle 142, a first microfiber head 144a, and a second microfiber head 144b. The third example swab 140 is similar to the second example swab 120, but in the third example swab 140, the length of the microfiber heads 144a-b is longer relative to the length of the handle 142. For example, the heads 144a-b can have a length equal to or longer than the handle 142.

The fourth example swab 160 includes a handle 162, a first microfiber head 164a, and a second microfiber head 164b. The fourth example swab 160 is similar to the first example swab 100, but in the fourth example swab 160, the heads 164a-b do not taper to the handle 162. For example, the heads 164a-b can be conically shaped and wider than the handle 162.

The fifth example swab 180 includes a handle 182, a first microfiber head 184a, and a second microfiber head 184b. Each head 184a-b includes three rounded protrusions, one away from the handle 182 in the direction of the handle and two perpendicular to the handle 182. This can be useful, e.g., in allowing the user to fit the surface area of the microfiber to the shape of a person's ears. The heads 184a-b can be formed, e.g., by wrapping a microfiber cloth around a cardboard structural component.

The five example swabs 100, 120, 140, 160, and 180 are examples of various microfiber swabs that can be useful in removing hair trimmings from a person's ears after a haircut. Swabs of other shapes and sizes can also be used.

The example swabs are generally sized so that the handles can be gripped by a a user's fingers and so that the microfiber heads can fit within the grooves of a typical person's ear. For example, the swabs can be 2-3 inches (5.08-7.62 cm) long and can have a width of 0.25-0.5 inches (0.64-1.27 cm). The microfiber heads can have a length of 0.25-0.5 inches (0.64-1.27 cm). The handle can have a width of 0.125-0.5 inches (0.32-1.27 cm). Where the handle is cylindrical, the width of the handle is the diameter of the cylinder.

The example swabs are illustrated as having two microfiber heads. This is useful, e.g., so that a barber or stylist can clean one ear with one microfiber head and then reverse the swab to clean the other ear with the other microfiber head. Although the example swabs are illustrated as having two heads, the swabs can be made to have only one head. In that case, a barber or stylist could use two swabs to clean both of a person's ears, or use the same head to clean both of a person's ears.

The microfiber cloth used on the swabs need not be made lint free and packaged to be made sterile. The swabs could be produced using microfiber suitable for consumer use, similar to cotton swabs. The microfiber cloth can be made without any solvents applications or other kind of chemicals which would not be suitable for application to a person's ears.

In addition to removing loose hair trimmings after a haircut, the swabs can be used to clean dust or moisture from various other surfaces. For example, the swabs can be used to clean: picture frame details and corners; car vents; stereo knobs, buttons, and flaps; computer keyboards; computer screen corners; eyeglass lenses, especially close to the nose piece and frames; gun sites; gun details on the surface of wood or plastic; filter grates; hair cutting tools for barbers, hair stylists, and animal groomers; faces that have unwanted makeup powder; camera lenses, buttons, and crevices; and ears after a shower.

Figure 2A:
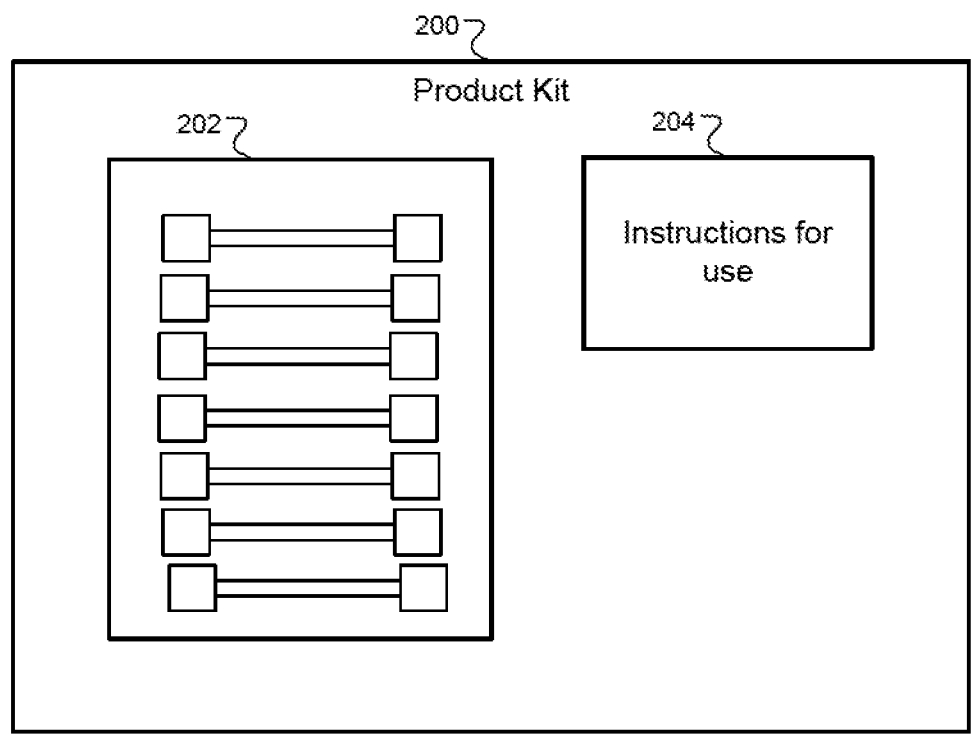

FIG. 2A is a diagram of an example product kit 200 that could be produced and sold to barber shops, hair salons, and the like. The kit 200 includes a number of microfiber swabs in a package 202, e.g., any of the example swabs 100, 120, 140, and 160 described above with reference to FIG. 1. The kit also includes instructions 204 for proper use of the swabs.

The instructions can be printed, e.g., on product packaging or a paper insert. The instructions can be a simple statement that the swabs can be used to clean loose hair trimmings from a person's ears or more the instructions can include further details on proper usage of the swabs. For example, the instructions can instruct a barber or stylist, e.g., on how to carefully apply a swab to a person's ears so as not to surprise the person or cause discomfort; on how to apply the swab to a person's ears to effectively remove most of the loose hair trimmings in and around the ear; on not inserting the swab into the ear canal; on the importance of using only one swab per person for hygiene reasons; and on how to politely ask for a person's permission to use the swab.

Figure 2B:
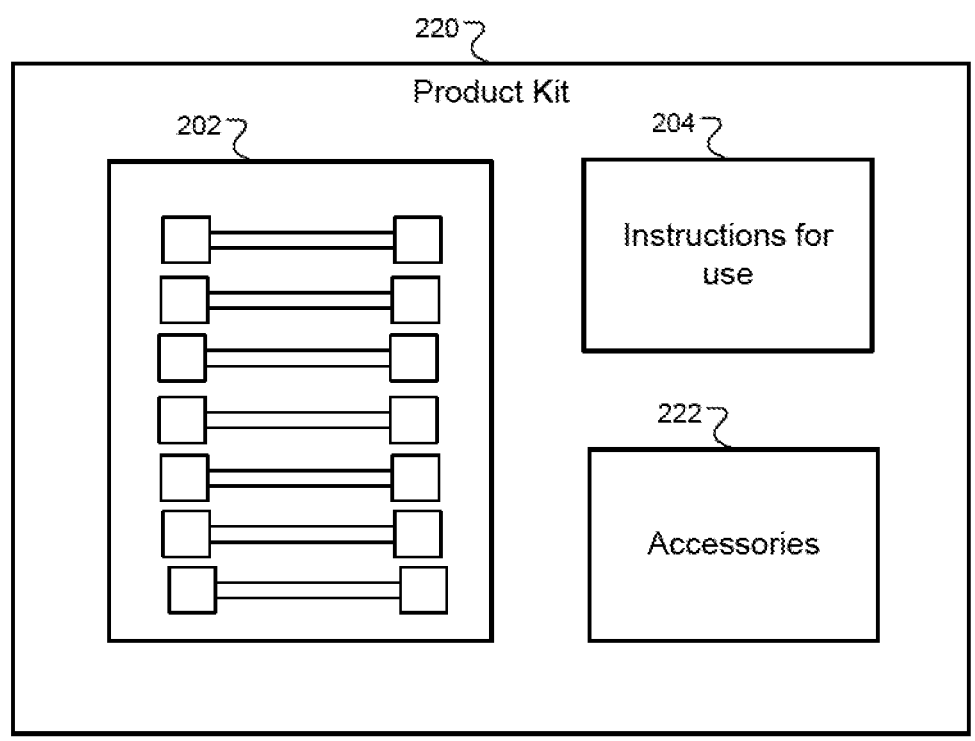
FIG. 2B is a diagram of a different example product kit that includes the package of swabs and the instructions for use and also other accessories.

FIG. 2B is a diagram of a different example product kit 200 that includes the package 202 of swabs and the instructions for use 204 and also other accessories 222. The accessories can be, e.g., larger microfiber clothes which can be used in a barbershop for cleaning various tools or customer's cloths. The accessories could also include other barbershop supplies, e.g., towels and neck strips, styling products, latherizer soap, and so on.

Figure 3:
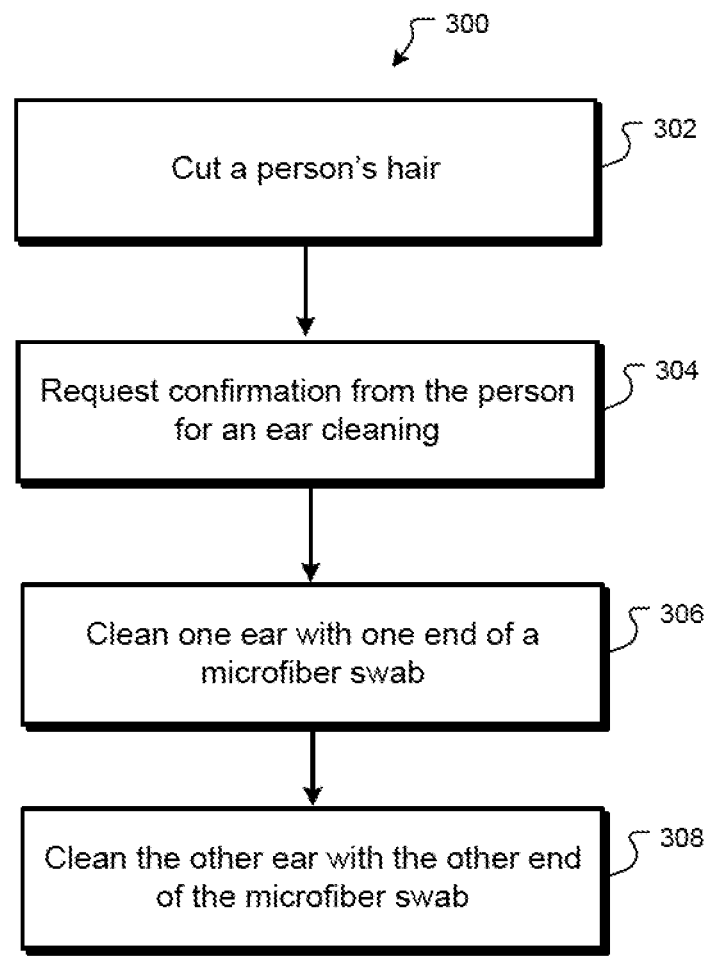
FIG. 3 is a flow diagram of an example process performed by a barber or hair stylist for cutting a person's hair and cleaning up loose hair trimmings.

FIG. 3 is a flow diagram of an example process 300 performed by a barber or hair stylist for cutting a person's hair and cleaning up loose hair trimmings. For purposes of illustration, the method is described as being performed by a barber, but the method can be performed by anyone who is cutting hair.

The barber cuts the person's hair 302. For example, the barber can use an electric trimmer, which inadvertently leaves a number of loose hair trimmings around the person's face and neck and in the person's ears. The loose hair trimmings can be from hair on the sides of the person's head or from the person's neck.

The barber can use conventional methods for removing loose hair trimmings, e.g., with a neck towel or brush or with a forced air system to blow away loose hair trimmings. Some loose hair trimmings will remain in the person's ear. Since it is uncomfortable to use a forced air system on a person's ear, and since conventional neck towels can be ineffective at removing loose hair trimmings, the barber can use a microfiber swab to remove loose hair trimmings from the person's ear.

The barber optionally requests confirmation from the person for an ear cleaning 304. Typically the barber will request confirmation from the person since it can be surprising to have a swab placed into a person's ear, but in some cases, e.g., where the barber knows that the person prefers an ear cleaning, the barber can proceed without requesting confirmation.

The barber then cleans one ear with one end of a microfiber swab 306. For example, the barber can use any of the example microfiber swabs 100, 120, 1406, and 160 described above with reference to FIG. 1. The barber cleans the outside of the ear, removing the loose hair trimmings without alarming the person or inserting the swab into the ear canal. The barber then cleans the other ear with the other end of the microfiber swab 308. If the barber is using swabs with only one microfiber head, the barber can use a different swab, or use a different side of the microfiber head to clean the other ear.

Figure 4A:
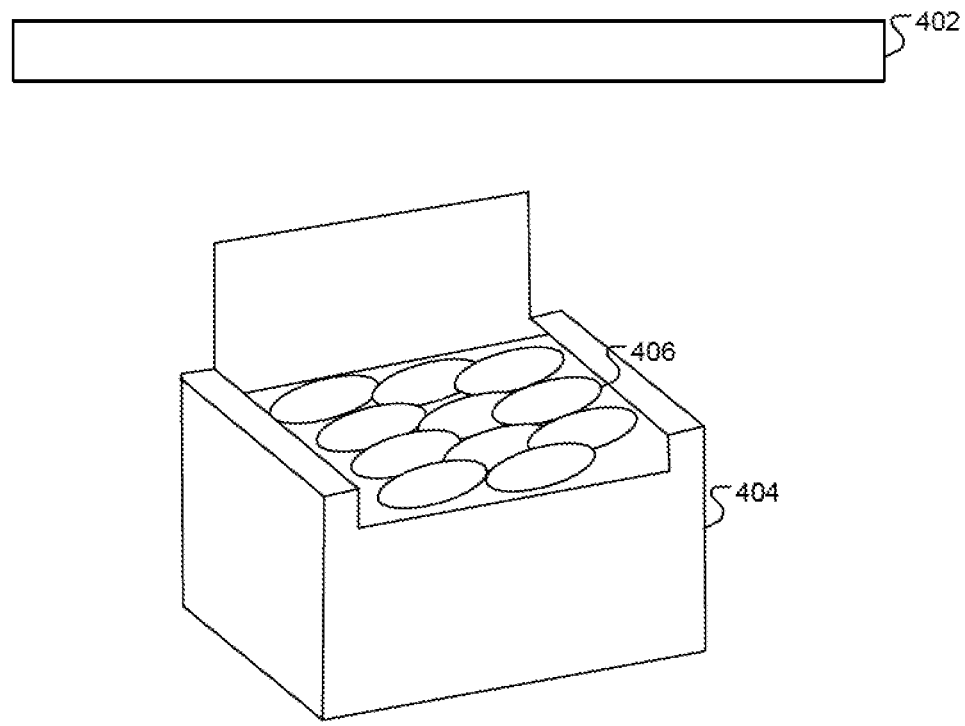
FIG. 4A is a diagram showing an example microfiber neck strip and a box of bundles of microfiber neck strips.
Figure 4B:
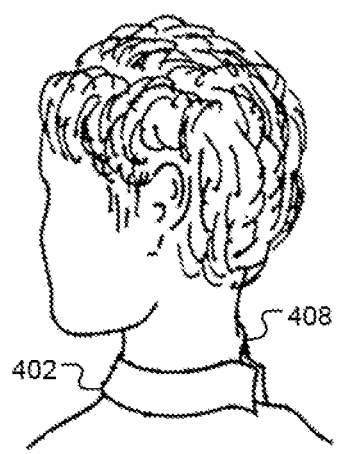
FIG. 4B is a view of a person who is getting a haircut.

FIG. 4A is a diagram showing an example microfiber neck strip 402 and a box 404 of bundles 406 of microfiber neck strips. FIG. 4B is a view of a person who is getting a haircut. A barber or stylist has placed a neck strip 402 onto the person's neck 408.

The neck strip 402 is made from a thin piece of microfiber cloth and is designed to be disposable, e.g., so that a barber or hair stylist can use a new, clean strip for each customer.

The microfiber cloth can be made from a synthetic fiber, e.g., polyester, or a blend of polyester and polyamide. The microfiber cloth will generally be split during the manufacturing process to produce multi-stranded fibers, leaving a structure with fiber spaces that can be loaded with loose hair trimmings or dust or other substances. The microfiber cloth will generally also be electrostatic, e.g., by being positively charged. Due to the charge, the microfiber cloth can attract other substances having an electrostatic charge, e.g., loose hair trimmings.

The neck strip 402 can be about 17 or 18 inches (43.18-45.72 cm) long and about two to three inches (5.08-7.62 cm) wide. The width is reduced as the neck strip is stretched out to be wrapped around a person's neck. The neck strip 402 can optionally include a pair of adhesive strips or mechanical tabs at both ends to assist in securing the neck strip 402 around a person's neck. The neck strip 402 can have serrated ends so that multiple strips can be detachably secured in a bundle 406.

The box 404 can be made of cardboard or any other appropriate material, and the box 404 can include an opening to provide easy access for barbers and hair stylists to new bundles. A barber or stylist can remove a bundle from the box and then detach strips individually so that a new strip can be used for each new customer.

Figure 5:
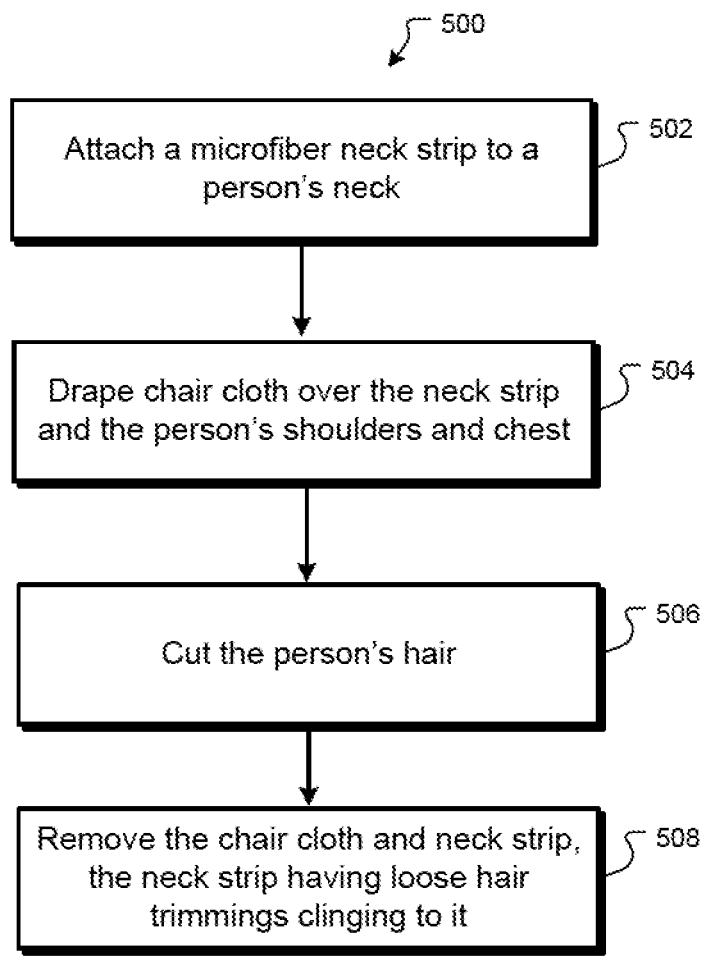
FIG. 5 is a flow diagram of an example process performed by a barber or hair stylist for cutting a person's hair and cleaning up loose hair trimmings.

FIG. 5 is a flow diagram of an example process 500 performed by a barber or hair stylist for cutting a person's hair and cleaning up loose hair trimmings. For purposes of illustration, the method is described as being performed by a barber, but the method can be performed by anyone who is cutting hair.

The barber attaches a microfiber neck strip to a person's neck 502. For example, after asking the person to be seated, the barber can detach the microfiber neck strip from a roll of microfiber neck strips. The barber wraps the strip around the person's neck and, in some cases, secures the two ends of the strip.

The barber drapes a chair cloth over the neck strip and the person's shoulders and chest 504. The chair cloth does not contact the person's skin and instead touches the neck strip. In some examples, the chair cloth has a fastener that closes and further secures the neck strip so that it does not fall out during the haircut.

The barber cuts the person's hair 506. While cutting the person's hair, loose hair trimmings may fall onto the microfiber neck strip. Because the neck strip is made from microfiber, it will attract the loose hair trimmings. This is useful, e.g., so that the loose hair trimmings are less likely to stay on the person's neck.

The barber removes the chair cloth and the neck strip 508. The neck strip has loose hair trimmings clinging to it that do not remain instead on the person's neck, which can give the person a cleaner appearance. The barber can then dispose of the neck strip.

The neck strips can also be used with the microfiber swabs described above with reference to FIGS. 1-3. For example, the neck strips can be packaged with the accessories 222 described in the product kit 220 of FIG. 2B. Alternatively, the neck strips can be packaged in a separate package with instructions for using the neck strip in accordance with the process 500 described in FIG. 5.

What is claimed is:

1. A method performed by a barber or hair stylist, the method comprising:
   providing a positively charged microfiber swab, the positively charged microfiber swab comprising:
   a handle having opposed first and second ends; and
   a first microfiber head secured to the first end of the handle, and a second microfiber head secured to the second end of the handle;
   each microfiber head defined by a respective solvent-free microfiber cloth, where the microfiber cloth is made from synthetic multi-stranded split fibers, positively charged and configured to attract and hold loose hair trimmings to spaces created between the split fibers;
   each microfiber head configured to fit within the grooves of a person's ear; cutting the person's hair, resulting in loose hair trimmings falling into the person's ears; and
   applying one of the first or second microfiber heads of the positively-charged microfiber swab to one of the person's ears to remove the loose hair trimmings resulting from cutting the person's hair, and
   applying the other of the first or second microfiber heads of the positively-charged microfiber swab to the other of the person's ears to remove loose hair trimmings.

2. The method of claim 1, wherein the first microfiber head comprises polyester or a blend of polyester and polyamide.

3. The method of claim 1, wherein the handle has a handle width and the first microfiber head has a head width, and wherein the handle width is smaller than the head width.

4. The method of claim 1, wherein the handle has a handle width and the first microfiber head has a head width, and wherein the handle width is greater than or equal to the head width.

5. The method of claim 1, wherein the microfiber swab has a length of 2-3 inches (5.08-7.62 cm) a width of 0.25-0.5 inches (0.64-1.27 cm).

6. The method of claim 1, wherein each of the first and second microfiber heads further comprise a shaped structure extending outwardly from the respective first and second ends of the handle, where the microfiber cloth is sealed to the shaped structure such that the first and second microfiber head assumes the shape of the shaped structure.

7. The method of claim 1, wherein the first microfiber head comprises a flat, bendable piece of microfiber cloth with rounded edges.

8. The method of claim 3, wherein the first microfiber head comprises polyester or a blend of polyester and polyamide, and the handle has a handle width and the first microfiber head has a head width, and the handle width is greater than or equal to the head width.

9. The method of claim 8, wherein the microfiber swab has a length of 2-3 inches (5.08-7.62 cm) a width of 0.25-0.5 inches (0.64-1.27 cm).

10. The method of claim 9, wherein the microfiber cloth of the first microfiber head comprises a piece of the microfiber cloth wrapped over the first end of the handle, and wherein the first microfiber head comprises a flat, bendable piece of microfiber cloth with rounded edges.

11. A product kit for sale to barbers or hair stylists, the product kit comprising:
    a plurality of positively-charged microfiber swabs, each positively-charged microfiber swab comprising:
        a handle having opposed first and second ends; and
        a first microfiber head secured to the first end of the handle, and a second microfiber head secured to the second end of the handle;
        each microfiber head defined by a respective solvent-free microfiber cloth, where the microfiber cloth is made from synthetic multi-stranded split fibers, positively charged and configured to attract and hold loose hair trimmings to spaces created between the split fibers;
        each microfiber head configured to fit within the grooves of a person's ear; and
    instructions for a barber or a hair stylist to, after cutting the person's hair, apply one of the first or second heads of the positively charged microfiber swab to one of the person's ears to remove the loose hair trimmings resulting from cutting the person's hair and subsequently applying the other of the first or second heads of the positively charged microfiber swab to the other of the person's ears to remove the loose hair trimmings.

12. The product kit of claim 11, wherein each first microfiber head comprises polyester or a blend of polyester and polyamide.

13. The product kit of claim 11, wherein each handle has a handle width and each first microfiber head has a head width, and wherein the handle width is smaller than the head width.

14. The product kit of claim 11, wherein each handle has a handle width and each first microfiber head has a head width, and wherein the handle width is greater than or equal to the head width.

15. The product kit of claim 11, wherein each microfiber swab has a length of 2-3 inches (5.08-7.62 cm) a width of 0.25-0.5 inches (0.64-1.27 cm).

16. The method of claim 11, wherein each of the first and second microfiber heads further comprise a shaped structure extending outwardly from the respective first and second ends of the handle, where the microfiber cloth is sealed to the shaped structure such that the first and second microfiber head assumes the shape of the shaped structure.

17. The product kit of claim 11, wherein each first microfiber head comprises a flat, bendable piece of microfiber cloth with rounded edges.

18. The product kit of claim 11, wherein each microfiber head comprises polyester or a blend of polyester and polyamide, each handle has a handle width and each microfiber head has a head width, and the handle width is greater than or equal to the head width.

19. The product kit of claim 18, wherein the microfiber cloth of each microfiber head comprises a flat, bendable piece of the microfiber cloth with rounded edges.

20. The product kit of claim 19, wherein each microfiber swab has a length of 2-3 inches (5.08-7.62 cm) a width of 0.25-0.5 inches (0.64-1.27 cm).

21. The product kit of claim 20, wherein each microfiber head is defined by the microfiber cloth wrapped over the respective end of the handle.

* * * * *